United States Patent [19]

Bertermann

[11] Patent Number: 5,290,538
[45] Date of Patent: Mar. 1, 1994

[54] NEPHRO PROTECTIVE INFUSION SOLUTIONS

[76] Inventor: Hagen Bertermann, Flensburger Strasse 83, D-2300 Kiel, Fed. Rep. of Germany

[21] Appl. No.: 873,579

[22] Filed: Apr. 21, 1992

Related U.S. Application Data

[63] Continuation of Ser. No. 566,365, Oct. 15, 1990, abandoned.

[30] Foreign Application Priority Data

Dec. 22, 1988 [DE] Fed. Rep. of Germany ....... 3843241

[51] Int. Cl.$^5$ .................... A61K 49/00; A61K 31/40; A61K 31/195
[52] U.S. Cl. ..................... 424/10; 514/423; 514/561; 514/922
[58] Field of Search .............. 514/561, 423, 922; 424/10

[56] References Cited

U.S. PATENT DOCUMENTS 2,376,795  5/1945  Martin ................................. 424/10
4,352,814 10/1982  MacKenzie ......................... 424/273

FOREIGN PATENT DOCUMENTS 0255722 12/1985 Japan .

OTHER PUBLICATIONS

Dyer, H. M. *An Index of Tumor Chemotherapy*, p. 147, Item #4242, Mar. 1949.

*Primary Examiner*—Frederick E. Waddell
*Assistant Examiner*—Gregory Hook
*Attorney, Agent, or Firm*—Herbert W. Larson

[57] ABSTRACT

The invention herein is a method of protecting against renal damage in a patient receiving carboplatin, cyclosporine A or cisplatin comprising administering to said patient the following mixture of amino acids consisting of glycine, L-alanine, L-serine, L-threonine, L-valine, L-leucine, L-isoleucine and L-proline.

8 Claims, No Drawings

NEPHRO PROTECTIVE INFUSION SOLUTIONS

This application is a continuation of Ser. No. 07/566,365, filed Oct. 15, 1990, now abandoned.

BACKGROUND OF THE INVENTION

This invention relates to nephroprotective infusion solutions. More particularly, it relates to the use of a mixture of L-amino acids in solutions to protect patients from nephrotoxic cytostatic and immunosuppressive agents.

PRIOR ART

Toxic renal damage constitutes a substantial side effect of cytostatic treatment of malignant tumors, while also excluding approximately one-third of patients from treatment. If renal elimination of cytostatic or immunosuppressive agents is delayed, further toxic damages may arise in other organs, particularly in the bore marrow, as a secondary result of nephrotoxicity. Efforts to reduce toxicity by increasing diuresis and/or urine flow do not prevent the occurrence of serious renal function impairment resulting from the administration of cytostatic or immunosuppressive agents. Thus, a reduction in kidney function often remains clinically undiscovered, as serum creatinine levels do not rise until more severe loss of renal function is reached.

It is a well-known procedure to treat renally insufficient patients from a nutritive standpoint with amino acid mixtures containing mainly essential L-amino acids. The mixtures of L-amino acids developed for this purpose, one of which is presented in DE 34 14 491 Al, however, may also have a detrimental effect on the kidneys. In individual cases they may induce acute renal failure or potentiate a preexisting acute renal failure.

The commonly known amino acid mixtures are not suitable for kidney protection against the toxic effects of cytostatic and immunosuppressive agents.

SUMMARY OF THE INVENTION

By means of the invention/development, blocking of a toxic increase in lysosomal activity in the proximal tubular cell must be achieved while a high glomerular filtration rate within the required dosage range of the mixture is maintained.

The invention/development will solve this problem/task by employing the mixture of different L-amino acids. The L-amino acids include L-glycine, L-alanine, L-serine, L-threonine, L-valine, L-leucine, L-isoleucine and L-proline. Through the produced blockage of lysosomal activity, the proximal tubular cell becomes reversibly insensitive to damage by cytostatic and immunosuppressive agents.

Intravenous access of the mixture recommended here prior to cytostatic treatment counteracts toxic renal damage resulting from cytostatic drugs or that resulting from immunosuppressive agents. The recommended amino acid mixture stabilizes renal filtration rate and augments energy production, in the tubular cell during early stage kidney damage by cytostatic and immunosuppressive agents. This cellular site of action prevents the progression from reduced cell function to irreversible kidney cell damage with subsequent total cell destruction.

Experiments have shown that mere variation of the solution according to DE 34 14 419 Al (which may be suggested at the reference location Ca 98 (1983):a 88 032 u; R. A. Zager et al., J. Lab. Clin. Med. (1983), 101, S. 130-140) does not lead to the desired result.

DETAILED DESCRIPTION OF THE INVENTION

The here recommended use is aimed at renally healthy individuals who risk being subjected to renal damage during treatment of another ailment. However, nutrition of the kidney is not an aim of the recommended mixture, as this is achieved by other means. Composition of the mixture is directed specifically at toxicity blockage thereby minimizing nitrogen load. Thus, the protective effect depends upon the relative concentrations of the employed amino acids.

Amino acid uptake into the kidney cell was investigated via metabolic effects considering individual amino acids as well as various combinations thereof. Suspensions of renal tubular segments incubated at 37° C. in oxygenated media served as the test material for these investigations.

Toxic kidney damage by cytostatic agents such as cisplatin and carboplatin essentially occurs at the proximal tubular cell, involving an intracellular site of action of unbound platin and its metabolites. The investigations within the scope of cisplating nephrotoxicity revealed activation of autophagia. Furthermore the present results suggest that autophagia is controlled by a regulatory mechanism modulated by L-amino acids. Surprisingly, pretreatment with some combinations of L-amino acids resulted in inhibitory modulation of the stimulated lysosomal autophagia while other combinations resulted in activating modulation following exposure to cisplatin and/or carboplatin. Only a limited concentration dependence is seen, which can be explained by the intracellular cumulative effects of amino acids. These arise due to more rapid transport kinetics across the (urine side) luminal membrane than across the (blood side) basement membrane. Parallel experiments have shown that stimulation of autophagia is linked to enzyme release, which itself causes regulatory damage to mitochondrial functioning and uncoupling of the respiratory chain (Example 1). Extensive mitochondrial damage inevitably leads to the destruction of proximal tubular cells.

The suggested use of neutral L-amino acids (Table 1) for nephroprotective purposes is based on modulation of intracellular autophagia in kidney cells. Activation of autophagia as a result of nephrotoxic effects is reversibly blocked if the described L-amino acid mixture is administered beforehand. the composition of the mixture is based on systematic investigations of proximal tubular cells from the kidney. The advantage of using a mixture comprised of different amino acids is the resultant maximum intracellular modulation effect achieved when several individual L-amino acids of the mixture cross the cell membrane via different transport channels and accumulate intracellularly.

Intact kidney cell function has proven to be a basic requirement for successful toxicity blockage. This may be due to the fact that an intracellular L-amino acid concentration optimal for a protective effect is generated by the cell itself through an active, energy-consuming cumulative process. Before the nephrotoxic effect of the cytostatic agent sets in, the modulation of lysosomal autophagia must have taken place. 18 hours are required for the induction of modulation. A marked augmentation of cell viability was observed in the presence of cytostatic agents if those amino acids given in Table 1 were added.

TABLE 1

| Amino Acid | g/l | mM/l |
|---|---|---|
| glycine | 9–11 | 120–146 |
| L-alanine | 12–17 | 135–191 |
| L-serine | 10–18 | 95–171 |
| L-threonine | 2–5 | 17–42 |
| L-valine | 5–10 | 43–85 |
| L-leucine | 6–10 | 46–76 |
| L-isoleucine | 2–4 | 15–30 |
| L-proline | 6–12 | 52–104 |

Under in vivo conditions the amino acid mixture given in Table 2 has proven to be particularly suitable with regard to renal filtration and reabsorption.

TABLE 2

| | g/l | mM/l |
|---|---|---|
| glycine | 11 | 146 |
| L-alanine | 15 | 168 |
| L-serine | 15 | 143 |
| L-threonine | 5 | 42 |
| L-valine | 10 | 85 |
| L-leucine | 10 | 76 |
| L-isoleucine | 4 | 30 |
| L-proline | 10 | 87 |

In contrast to the augmentation of cell viability using the mixtures of L-amino acids given in Table 1 involving the suppression of autophagia in the kidney cell, a principally vascular site of action with a delimited concentration range underlies the stimulation of glomerular filtration by these mixtures.

One of the mixtures of neutral L-amino acids as given in Table 2, developed for nephroprotection during chemotherapy based on these results, was . applied in several patients (c.f. Example 2, Sol. III). 200 g of the mixture per 24 hours were continuously infused such that a nearly constant serum amino acid concentration was achieved over the entire treatment period. The investigations revealed an efficacious nephroprotection against toxic effects of chemotherapy in those patients preliminarily treated as described. A control group received the same dosage of a commercially available amino acid solution (c.f. Example 2, So. I) during chemotherapy with the composition (ng/l) as given in Table 3.

A further control group was treated (under otherwise analogous conditions) with a modification of the mixture given in Table 3 which lacked the acidic and alkaline amino acids of the Sol. I mixture (c.f. Example 2, sol. II).

TABLE 3

| | g/l |
|---|---|
| L-isoleucine | 5.1 |
| L-leucine | 8.9 |
| L-lysine | 7.0 |
| L-methionine | 3.8 |
| L-phenylalanine | 5.1 |
| L-threonine | 4.1 |
| L-tryptophan | 1.8 |
| L-valine | 4.8 |
| L-arginine | 9.2 |
| glycine | 7.9 |
| L-alanine | 13.7 |
| L-asparagine | 3.7 |
| L-aspartic acid | 1.3 |
| L-cysteine | 0.7 |
| L-glutamic acid | 4.6 |
| L-ornithine | 3.2 |

TABLE 3-continued

| | g/l |
|---|---|
| L-proline | 8.9 |
| L-serine | 2.4 |
| L-tyrosine | 1.3 |

The control groups (sol. I and sol. II) showed a stable glomerular filtration performance over a maximum of 3 days, followed by a considerable drop in filtration rate, a decrease in tubular reabsorption, while tubular enzyme losses were multiplied during platin-based therapies.

The omission of potentially nephrotoxic anionic and cationic amino acids (i.e. acidic and basic) from the mixture given in table 3 showed no measurable protective effects on renal function during chemotherapy compared to the equivalent dosage of the commercially available mixture given in Table 3 (c.f. Example 2, Sol. II).

On the other hand, the mixture presented in Table 2 (Sol. III) was distinguished in application in patients by increased renal filtration for the duration of chemotherapy, a normal salt reabsorption and a nearly complete normalization of tubular enzyme leakage. Patients with renal insufficiency who, without nephroprotection, would have been excluded from chemotherapy because of the side effect of impending renal failure, showed no measurable nephrotoxic effects. Additionally, a substantial improvement in renal glomerular filtration rate compared with the baseline performance and a decrease in serum creatinine concentration were observed using the L-amino acid mixture represented in Table 2 (Sol. III). To evaluate the effect of the recommended mixture on kidney cell functioning a newly developed urine enzyme analysis was used, along with the commonly used methods of the clinic, which exhibits a considerably greater sensitivity for detection of renal cell dysfunction. The blocking of toxic renal cell damage in the group protected by means of the recommended L-amino acid mixture was clearly demonstrable using the highly sensitive urine enzyme analyses (c.f. Example 2).

Because the mixture in Table 2 is a combination of neutral amino acids, exclusively, practically no solution imbalances arise. For practical clinical reasons the amino acids are dissolved into a 0.45% sodium chloride solution in which chloride is partly replaced by aspartate while controlling pH values.

| Amino Acid | g/l | mM/l |
|---|---|---|
| glycine | 11 | 146 |
| L-alanine | 15 | 168 |
| L-serine | 15 | 143 |
| L-threonine | 5 | 42 |
| L-valine | 10 | 85 |
| L-leucine | 10 | 76 |
| L-isoleucine | 4 | 30 |
| L-proline | 10 | 87 |
| sodium chloride/aspartate | 4.5 | 80 |
| Total | 85 | 857 |

The mixtures in Tables 2 and 4 showed a nephroprotective efficacy against nephrotoxic cytostatic (Example 2) and immunosuppressive pharmaceutical agents (Example 3). Observations revealed that even the side effects of other chemotherapeutic agents, themselves not nephrotoxic but mainly renally excreted, on other organs, e.g. the haematogenic system, were suppressed by the above mentioned L-amino acid mixtures.

The following examples set forth the invention in still greater detail.

EXAMPLE 1

Relation of the release of autophagic enzyme activity to regulatory disorder of respiratory mitochondrial function Isolated proximal tubular segments (ITS) from rat kidneys were exposed to different concentrations of cisplatin, were then washed and reincubated cisplatin-free (both periods lasting 20 min). the ITSs were suspended in Ringer's solution containing albumin (10%) to which glucose (gluc) and amino acids (AA) were added as substrates. The observed leakage rates of N-acetyl-B-D-glucosaminidase (NAG) during the reincubation period were assigned to the mitochondrial acceptor control index (ACI) determined after the incubation period. ITSs incubated cisplatin-free served as controls.

Gluc: 18 mM/l, Gluc+AA: 10 mM/l Glucose+8 mM/l total of glycine, alanine, serine, threonine, valine, leucine, isoleucine and proline.

n=12, x±SEM.

| TEST | MEDIUM | NAG [u/g protein/min] | ACI [±ADP] |
|---|---|---|---|
| | Gluc + AA | 4.3 ± 0.7 | 7.2 ± 1.4 |
| Control | Gluc | 4.7 ± 0.7 | 6.8 ± 1.2 |
| Cisplatin | Gluc ± AA | 10.3 ± 1.8 | 5.8 ± 1.0 |
| (5 mg/100 ml) | Gluc | 17.5 ± 2.9 | 5.1 ± 0.8 |
| Cisplatin | Gluc + AA | 31.3 ± 5.4 | 1.9 ± 0.3 |
| (10 mg/100 ml) | Gluc | 35.2 ± 5.6 | 1.4 ± 0.3 |

EXAMPLE 2

Blocking of nephrotoxic effects of platin derivatives by means of nephroprotective L-amino acids In 60 patients parameters of tubular (N-acetyl-B-D-glucosamini-dase, [NAG], cumulative) and glomerular (glomerular filtration rate [GFR], renal function were measured prior to (internal controls) and during cytostatic treatment with cis- and carboplatin. One group of 12 patients received preliminary treatment with a nephroprotective mixture according to Table 2 (Sol. III). another group of 12 patients were treated with a commercially available, conventional amino acid mixture as given in Table 3 (Sol. I). A third group of 12 patients received a modification of the mixture according to Table 3 which lacked the components glutamic acid, aspartic acid, asparagine, arginine, lysine and ornithine (sol. II).

x±SEM.

| Cytostatic agent | Amino Acid Mixture | Cumulative NAG [Units] | GFR [ml/min] |
|---|---|---|---|
| | internal control | 17.2 ± 2.4 | 115 ± 14 |
| Cisplatin | Sol. I | 56.1 ± 7.1 | 55 ± 12 |
| | Sol. II | 58.5 ± 6.3 | 59 ± 12 |
| | Sol. II | 29.5 ± 4.9 | 180 ± 21 |
| | internal control | 17.5 ± 2.3 | 112 ± 12 |
| Carboplatin | Sol. I | 38.3 ± 5.4 | 68 ± 11 |
| | Sol. III | 21.3 ± 3.9 | 186 ± 19 |

EXAMPLE 3

Blocking of the nephrotoxic effects of cyclosporine A by means of nephroprotective L-amino acids Parameters of tubular (N-acetyl-B-D-glucosminidase, [NAG], calculated as U/g creatinine in urine) and glomerular (glomerular filtration rate, [GFR]) renal function were measured in 30 organ transplant patients prior to (internal control) and during immunosuppressive therapy with cyclosporine a. 10 patients received a preliminary treatment with a nephroprotective amine acid mixture as given in Table 2 (Sol. III). Another 10 patients were treated with a commercially available, conventional amino acid mixture per Table 3 (Sol. I). An additional 10 patients received a modification of the mixture represented in Table 3 which lacked the components L-glutamic acid, L-aspartic acid, L-asparagine, L-arginine, L-lysine and L-ornithine (Sol. II).

x±SEM

| Immunosuppressive agents | Amino Acid Mixture | NAG i.U. [U/g creatinine] | GFR [ml/min] |
|---|---|---|---|
| | internal control | 2.8 ± 1.2 | 115 ± 14 |
| Cyclosporine A | Sol. I | 23.1 ± 3.4 | 76 ± 12 |
| | Sol. II | 24.5 ± 3.7 | 74 ± 12 |
| | Sol. III | 12.5 ± 2.6 | 172 ± 22 |

I claim:

1. Method of protecting a patient from renal damage caused by nephrotoxic effects of a cancer chemotherapeutic or immunosuppressant agent comprising administering intravenously to the patient in association with the cancer chemotherapeutic agent or immunosuppressant agent selected from the group consisting of carboplatin, cyclosporine A and cisplatin a pharmaceutically acceptable solution containing a nephroprotective amount of the following mixture of amino acids consisting of 9 to 11 grams/liter of glycine,
12 to 17 grams/liter of L-alanine,
10 to 18 grams/liter of L-serine,
2 to 5 grams/liter of L-threonine,
5 to 10 grams/liter of L-valine,
6 to 10 grams/liter of L-valine,
2 to 4 grams/liter of L-isoleucine, and
6 to 12 grams/liter of L-proline.

2. A method according to claim 1 wherein the cancer chemotherapeutic agent is carboplatin.

3. A method according to claim 1 wherein an immunosuppressant agent is cyclosporine A.

4. A method according to claim 1 wherein the cancer chemotherapeutic agent is cisplatin.

5. A method according to claim 1 wherein the mixture of L-amino acids is administered intravenously in an aqueous solution.

6. A method according to claim 1 wherein the mixture of L-amino acids is administered intravenously dissolved in a sodium chloride solution.

7. A method according to claim 6 wherein about 25% by weight of the chloride of the sodium chloride solution is replaced by about 20 m Mol/l aspartate while controlling pH values within the range of 6.5 to 7.0.

8. A method according to claim 6 wherein the solution is 0.45% by weight sodium chloride.

* * * * *